(12) United States Patent
Lamattina et al.

(10) Patent No.: US 6,242,384 B1
(45) Date of Patent: Jun. 5, 2001

(54) METHOD OF ENHANCING THE METABOLIC FUNCTION AND THE GROWING CONDITIONS OF PLANTS AND SEEDS

(76) Inventors: Lorenzo Lamattina, Elcano 6374; Maria Veronica Beligni, Garcia Lorca 444, Dto. 3; Carlos Garcia-Mata, Roca 1646; Ana Maria Laxalt, Rivadavia 31, all of Mar Del Plata (AR)

(*) Notice: Subject to any disclaimer, the term of this patent is extended or adjusted under 35 U.S.C. 154(b) by 0 days.

(21) Appl. No.: 09/450,192

(22) Filed: Nov. 29, 1999

(30) Foreign Application Priority Data

Jul. 21, 1999 (AR) ............................................... 990103599

(51) Int. Cl.[7] ........................... A01N 33/04; A01N 37/02; A01N 37/30; A01N 59/00; A01N 59/16
(52) U.S. Cl. ........................... 504/187; 504/188; 504/319; 504/320; 504/326; 504/350
(58) Field of Search ........................... 504/188, 187, 504/319, 320, 326, 350

(56) References Cited

PUBLICATIONS

J.B. Hibbs, Jr. et al.; Nitric Oxide: A cytotoxic Activated Macrophage Effector Molecule; Biochemical and Biophysical Research Communications, vol. 157, No. 1, Nov. 30, 1988, pp. 87–94.

L.J. Ignarro; Biosynthesis and Metabolism of Endothelium–derived Nitric Oxide; Annu. Rev. Pharmacol Toxicol, 1990, pp. 535–560.

S.H. Snyder; Nitric Oxide: First in a New Class of Neurotransmitters?; Science, vol. 257, Jul. 24, 1992; pp. 494–496.

T. Noritake, et al.; Nitric Oxide Induces Phytoalexin Accumulation in Potato Tuber Tissues; Plant Cel Physiol. 37(1) 1996; pp. 113–116.

S. Pheiffer, et al., Detection of Nitric Oxide–Sensitive Guanylyl Cyclase in Higher Plants; Journal of Endothelial Cell Research, Abstracts of the Fourth International Meeting of Biology of Nitric Oxide Sep. 17–21, 1995, p. 66.

S. Shukdeb et al.; Nitric Oxide Synthase and Calmodulin Immunoreactivity in Plant Embroyonic Tissue; Biochemical Archives, vol. 11, 1995; pp. 221–227.

Y.Leshem et al.; The Characterization and Contrasting Effects of the Nitric Oxide Free Radical in Vegetative Stress and Senescence of *Pisum sativum* Linn. Foliage; J. Plant Physiol. vol. 148 1996; pp. 258–263.

J. Filep et al.; Nitric Oxide Co–Operates with Hydrogen Peroxide in Inducing DNA Fragmentation and Cell Lysis in Murine Lymphoma Cells; Biochem. J. 321 1997, pp. 897–901.

D. Wink et al.; Nitric Oxide Protects Against Cellular Damage and Cytotoxicity from Reactive Oxygen Species; Proc. Natl. Acad. Sci, USA vol. 90, Nov. 1993, pp. 9813–9817.

O. Sergent et al.; Effect of Nitric Oxide on Iron–Mediated Oxidative Stress in Primary Rat Hepatocyte Culture; Hepatology 25 1997; pp. 122–127.

A. Laxalt et al.; Nitric Oxide Preserves the Level of Chlorophyll in Potato Leaves Infected by *Phytophthora infestans*; European Jounal of Plant Pathology 103, 1997; pp. 643–651.

Y. Yoshie et al.; Nitric Oxide Synergistically Enhances DNA Strand Breakage Induced by Polyhydroxyaromatic Compounds, but Inhibits that Induces by the Fenton Reaction; Archives of Biochemistry and Biophysics, vol. 342, No. 1, Jun. 1, 1997; pp. 13–21.

M. Beligni et al.; Nitric Oxide Counteracts Cytotoxic Processes Mediated by Reactive Oxygen Species in Plant Tissues; Planta 1999 208; pp. 337–344.

M. Beligni et al.; Nitric Oxide Protects Against Cellular Damage Produced by Methylviologen Herbicides in Potato Plants; Nitric Oxide: Biology and Chemistry, vol. 3, No. 3, 1999; pp. 199–208.

*Primary Examiner*—S. Mark Clardy
(74) *Attorney, Agent, or Firm*—Norris, McLaughlin & Marcus PA

(57) ABSTRACT

A method of using nitric oxide (NO) to enhance crop performance at any stage of its development including sowing, growth, flowering, fruit formation or during many processes associated with the handling of the culture, such as transplantation, root formation in stem cutting, or any other handling that could involve an oxidative stress condition for the plants. The NO application according to the invention has also enhanced the chlorophyll levels thus resulting in a better photosynthetic capacity of the plant cells and also of protective pigments such as anthocianins and flavonoids.

16 Claims, No Drawings

METHOD OF ENHANCING THE METABOLIC FUNCTION AND THE GROWING CONDITIONS OF PLANTS AND SEEDS

BACKGROUND OF THE INVENTION

1. Field of the Invention

The present invention relates to methods of enhancing the growing process of vegetables, preferably living vegetables, most preferably living plants and/or seeds, and in general the invention is applicable to several fields of plant growing such as extensive and intensive agriculture, biotechnology, forest engineering, horticulture and gardening. The invention involves the use of nitric oxide (NO) to improve, enhance and/or increase the crop performance during any of the stages in the crop culturing, including sowing, growth and development, flowering and fruit formation or during any process associated with culture handling, such as transplantation, rooting, and other activity that could involve or lead to stress conditions for the plants and seeds.

To the purpose of the present specification, all the times that reference is made to the application of the invention to plants it is meant that the invention is broadly and generically applied to vegetables and plants in their broadest definition, including vegetables, plants, stem cutting, plantlets and seeds, preferably in a living state.

2. Description of the Prior Art

It is well known that the nitric oxide (NO) is an endogenous free radical formed in a variety of cell types by NO-synthase. Several roles and applications have been described for NO in animals (Hibb et al., Biochem. Biophys. Res. Commun., 157: 87–94, 1988; Ignarro et al., Annu. Rev. Pharmacol. Toxicol. 30: 535–560, 1990 and Snyder, S. H. Science 257: 494, 1992).

Evidence has been reported to demonstrate that NO may also be part of the functional complexity in the plant kingdom, thus, some publications and works have been referred to this matter such as the accumulation of potato phytoalexins by application of a NO-releasing compound (Noritake et al., Plant Cell Physiol. 37: 113–116, 1996); the presence of NO/cyclic guanylyl monophosphate (cGMP)-sensitive transduction pathway in potato (Pfeiffer et al., J. Endothelial Cell Res. Vol. 3, Abstract 66, 1995); and western blot analysis revealed positive immunoreactivity with rabbit anti-brain Nitric Oxide Synthase (NOS) antibodies in pea embryonic axes and wheat germ (Sen et al., Biochem. Arch. 11: 221–227, 1995).

In senescing pea foliage NO emission was promoted by the addition of an ethylene precursor whereas in rapidly growing pea foliage three NO-releasing compounds inhibited expansion, this being suggested as a new pathway in the regulation of plant growth (Leshem et al., J. Plant Physiol. 148: 258–263, 1996).

The WO 99/15022 discloses a method for reducing the rate of deterioration of perishable horticultural produce by the use of NO. This method is applicable in fruit, vegetables and/or flowers during post-harvest handling, storage and marketing. This WO Document remarks that the application of nitric oxide at low concentrations has been found to reduce the production of ethylene by young, growing vegetative cells from epidermis and foliar cells.

Both toxic and protective activities for NO have been demonstrated in different cellular systems. Toxic effects have been predominantly observed at high NO concentrations, in human immunological system for example, where a high NO production also has been described (Filep et al., Blood 87: 5136–5143, 1997). On the other side, in systems where toxicity comes mainly from the generation of other free radicals, like reactive oxygen species, NO can provide protection against cellular damage. This is accomplished by NO ability to scavenge ROS and, therefore, end chain-propagate reactions (Wink et el., Proc. Natl. Acad. Sci. USA 90: 9813–9817, 1993). NO reduced cell death produced in several systems, especially when mediated by the Fenton reaction (Sergent et al., Hepathology 25: 122–127, 1997 and Yoshie et el., Arch. Biochem. Biophys. 342: 13–21, 1997). Moreover, NO preserves the level of chlorophyll and diminishes cell death in potato leaves infected by Phytophthora infestans (Laxalt et al., Europa J. Plant Pathol. 103: 643–651, 1997).

It would be therefore convenient to have a method, based in the application of nitric oxide, for enhancing the metabolic functions and growing process of plants and seeds that result in better developments and productions of plants, in the agricultural field, for example.

SUMMARY OF THE INVENTION

It is therefore one object of the present invention to provide a method of enhancing the metabolic process and functions as well as the growing process and conditions of plants, also increasing the chlorophyll level and the dry matter of the plants, also the rooting of stem cutting, the process being based in contacting the plant with nitric oxide (NO). The method may be applied not only to plants but also to seeds with the purpose of enhancing the germination and facilitate the early developments of the plantlets.

It is still another object of the present invention to provide a method of enhancing the metabolic function and the growing conditions of plants, such as plants and stem cutting under culturing, plants and seeds under germination, wherein the dry matter and the productive yield of the plant is increased and the germinating capacity of the seed is enhanced, the method comprising the step of contacting the plant or the seed with nitric oxide or any NO-releasing chemical.

It is a further object of the present invention to provide a method of enhancing the growing as well as the productive capacity of plants and seeds, capable of being applied to any kind of plant including such plants obtained under intensive or extensive culturing, in the agriculture area, or in green houses, the method being also applied to plants obtained under micro propagation techniques, plants obtained through stem cutting, transgenic plants, monocotyledons, dicotyledons and gymnosperms. The method is proper and recommended to be applied in plants cultured under stress conditions, such as low temperatures, soils having high salinity, lack of water, drought, infection by organisms, herbicides, etc.

It is even another object of the present invention to provide a method of enhancing the growing process, the resistance and productivity of plants and seeds by applying to the plants and seeds NO generated by compounds, compositions, etc., generally known as NO-releasing chemicals, wherein the NO is used preferably in concentrations between about 10 nM and about 1 $\mu$M and may be applied, either to plants or seeds, by several application techniques such as aspersion, fumigation, immersion, irrigation, soil fertilization, etc.

The above and other objects, features and advantages of this invention will be better understood when taken in connection with the following description which is given as exemplary and no limitative.

DESCRIPTION OF THE PREFERRED EMBODIMENTS

The inventive method has been developed based in the studies of the plants that are usually subjected to adverse environmental conditions such as cold, freezing, water deficit, drought, dangerous light radiations, pathogens, light deficit, etc. During a crop culture, these situations can extremely affect the crop performance, these effects being evidenced by a loss of fresh and dry weights, necrosis, chlorosis and consequently a decrease in the quality and quantity of produce, such agricultural and horticultural produce.

The main mechanism by which these environmental conditions cause damage to crops and plants is the generation of reactive oxygen species (ROS), which species subject the plants to an oxidative stress. ROS produce a severe plant cell injury at the molecular level that includes lipid and protein peroxidation, RNA degradation, ion leakage, DNA fragmentation and cell death, all of which leads and result in a severe deterioration of the plant at the macroscopic level.

Oxidative stress is considered one of the most important causes of illness and aging, both in animals and plants. In humans, an important part of therapeutics is now directed to find better antioxidants that allow the human beings to be healthier so as to bear illnesses. According to the investigations and studies carried out by the inventors the above concept could be transferred to plants, wherein the antioxidant compounds could help the plants create a healthy endogenous status and hence increase the tolerance and resistance to adverse conditions. In this sense, nitric oxide (NO) has proven to be a powerful antioxidant and to protect a great variety of plant species against different stress conditions. These stress conditions include: drought, high salinity, herbicides, chilling, temperatures below 0° C., low irradiance, UV radiation, light excess, presence of heavy metals, heat shock, pollution, ozone presence, mechanical and physical damage and infection by pathogenic agents. It is quite Probable that the NO provides protection against stress by its ability to capture ROS and thus diminishes ROS-mediated toxic consequences. NO has also proven to enhance chlorophyll levels, which ends up in a better photosynthetic capacity of the plant cells and of the protective pigments such as anthocianins and flavonoids. Even at nanomolar amounts, NO prevent the plants from deterioration generated by such stress conditions to a surprising extent.

Up to now, NO has not been considered neither disclosed as being used for enhancing the growing process of plants and seeds and for increasing tolerance of the plants and seeds to stress situations, and the inventors have found this is of great relevance for improving crop yield, for example. The low cost of sodium nitroprusside (an NO-donor) and the power of NO at nM concentrations could enable the breeder to obtain very good results for a very cheap price. Moreover, the inventors have found and shown excellent results with some of the most important crops for human nutrition, including wheat, corn, potato and tomato and with other plant species frequently used in agriculture, horticulture, biotechnology, forestry, ornamentation and gardening. This marks up the potential of NO protection against many non-related plant species like monocots, dicots and gymnosperms.

The NO for use in this invention may be generated by NO donors, molecules that release No into solution.

There are many NO donors commercially available that greatly differ in their cost and technical properties:

* Nitrosothiols: -S-nitroso-N-acetylpenicillamine (SNAP)-S-nitrosoglutathione
* Nonoates:
  spermine-NO
  diethylamine-NO
  DETA-NO (NOC 18)
  PAPA-NO
  dipropylenetriamine-NO
* Sodium nitroprusside (SNP)
* SIN-1 chloride
* Hyponitric acid, disodium salt (Angeli's salt)

In general, all these donor agents exert their effect in a relatively rapid or quick fashion, which varies from hours to days. Very goods results may be obtained by preferably using SNP and SNAP.

From 3 to 4 spaced applications may be carried out on preventive basis during the development cycle of the culture by aspersing about 150 liters/hectare of SNP 100 $\mu$M. In green houses 5 liters of SNP 100 $\mu$M per 10 m$^2$ of plants may be aspersed. The number of applications may be increased to six (6) or seven (7) applications to increase the yield or production of the culture under some stress situation. It has been observed that the NO releasing is gradual and begins at the 2 hours after application.

Most of the earth planet surface is exposed to periods of low and very low temperature wherein it would be necessary and important to reduce the looses and limitations of the agricultural production. In view of such chilling periods an important part of the earth surface can not be used for agricultural purposes.

All the stages in the cycle of life in the plants, such as germination, growing, flowering or florescence, are affected by low temperatures and, while the plant may be not damaged, the development delay and extension of the plant life cycle is of very high importance from the agronomic point of view. The effects of chilling in the plants are associated with water deficiencies. Low temperatures may induce a temporary hydric deficit in the plant. The water absorption through the roots is severely restricted when the temperature decreases. When the temperature is low but not enough to form ice in the vegetable tissues, the known chilling injury is produced. This injury includes general lesions in the cell membrane.

The vegetable sensitivity to cold varies depending on main parameters such as the plant species, age, history of the individual plant and the environmental conditions. Generally the younger plants are the most sensitive. The sensitivity also differs for different organs, while the germinating seeds and the flowers are the most affected by low temperatures, the dormant seeds are the most resistant. This is why a late freezing weather in springtime and an early freezing weather in autumn are particularly dangerous.

The inventors have found, according to the invention, that the NO increases the tolerance against low temperature stress in plants and seeds. The pre-treatment of tomato plantlets (*Lycopersicum esculentum* sp.) by aspersion with Sodium nitroprusside (SNP) 100 $\mu$M, 24 hours before placing the tomato plantlets into a cold chamber at 4° C., and the post treatment with SNP for 90 days and under the same low temperature conditions, enabled the plantlets to complete the growing cycle when placed, after the chilling period, under a recovering temperature of 18° C. None of the plants treated with control solutions could be recovered. This demonstrates that the treatment with NO donor compounds protects the plantlets. particularly those more sensitive plantlets, against the chilling or cold effect. Said treatment may be used preventively when cold weather is expected or during cold periods of time, for example, to provide additional protection.

The pre-treatment by aspersion according to the present invention enabled corn and wheat plantlets to resist against chilling temperatures of −4° C. The recovering of plantlets treated with NO was notably superior to the recovering of those no-treated plants, i.e. control plants. One week after the stress under a temperature of −4° C. the plantlets treated with NO developed a foliaceous area 40% larger than the foliaceous area of the control plants. According to the invention, the pre-treatment of the cultures and crops would enhance the resistance of the plants against the chilling or freezing weather, thus increasing the number of plants that are capable of surviving to these cold conditions and also increasing the recovering capacity of the damaged plants.

The sweet corn grains (Zea mais sp Canner Hybrid) also shown resistance to chilling. The grains germinating in $NO_2^-/NO_3^-$ and $H_2O$ (control) shown a paralyzation in the germination process, combined with a withered condition of the radicle and the hypocotyl, while those germinating in SNP shown a continuous growing.

According to another aspect of the invention the resistance of wheat plants against the hydric stress when treated with NO has been demonstrated. To this purpose, a group of plants has been treated with SNP 100 $\mu$M and control groups were irrigated with $NO_2Na$ 10 $\mu$M plus $NO_3Na$ 10 $\mu$M, or with $H_2O$. At 12 days from the beginning of the treatment the plantlets were cultured without water until permanent withered symptoms appeared. In all of the cases the control plants shown a shortening of the normal cycle entering a phase of early flowering or florescence. The plants treated with SNP completed their cycle normally and provided a grain yield 30% higher that the plants under control treatment.

It is well known the important incidence of a correct and proper regulation of the florescence in the quantity and quality of the agricultural produces.

In like manner, when potato leaves (Solanum tuberosum sp. Cv. Pampeana) were subject to hydric stress, the treatment with NO enabled the plants to retain the chlorophyll levels at their normal values.

The treatment with NO allows the cultures to be successfully carried out in areas with arid and dry soils and during dry and drought periods.

Fungus are considered and recognized by the farmers as one of their main enemies. In the case of the cereal or grain plants, for example, it has been estimated that the 27% of the looses are due to fungus pathogens.

No visible effects have been observed when using NO on potasto leaves infected by the fungus Phytophora infestans (Mont.) of Bary, the late blight disease agent. The results show that chlorophyll levels are strongly maintained by NO in infected potatoes leaves. Nitric oxide was able to diminish apoptotic DNA fragmentation and ion leakage in infected potato leaves. These results have been obtained by immersing the potato leaves into 100 $\mu$M SNP solution or in a solution of 100 $\mu$M ascorbic acid+$NO_2Na$ 200 $\mu$M.

In addition to the foregoing, the NO can strongly protect plants against methylviologen damage and others herbicides that cause oxidative stress. NO diminishes symptoms of chlorosis, necrosis, and defoliation generated by Diquant in whole potato plants, and protect potato leaves from Diquat-induced ion leakage, lipid and protein peroxidation, chlorosis and necrosis.

It is well know that the UV radiation and high light fluxes (hlf) produce reactive oxygen species (ROS) that damage the cellular structures of the plants. Certain pigments like the flavonoids protect the plants against the harmful and destructive effect of the UV radiation. By employing the method of the invention, that is, by pre-treating potato plant leaves (Solanum tuberosum sp. Cv. Pampeana) with NO, the toxic action of the UV radiation has been diminished. The tissues of the leaves pre-treated and irradiated with SNP resulted undamaged and healthy as well as such leaves shown an 80% increasing in quantity of flavonoids as compared to the control leaves.

It is also known that photosynthetic organisms need sunlight to live and they are inevitably exposed to UV radiation. This radiation describes the spectral range of electromagnetic radiation (200–400 nm) which borders on the visible range of light. Less than 7% of the sun's radiation incident on the earth's surface is in the UV range of 295–400 nm. All shorter UV wavelengths are filtered by the ozone layer of the stratosphere. However, due to a dramatical reduction in the protective ozone layer by man-made toxic materials, the UV-B light has a disproportionally damaging effect to crops. UV-sensitive target include DNA, proteins and membranes, and these elements must be protected for normal plant growth and development. The main source of toxicity due to UV seems to come from an oxidative stress to which the irradiated plant is subjected. It has also been seen that plants growing in darkness or in UV-free white light react very sensitively to long-wave UV. This effect forms the basis of the "transplanting shock" which is usually suffered by young plants grown under UV-impermeable glass and then transplanted into open fields. Thus, transient wilting, bleaching and inhibition of development are observed. Then, plants became resistant and this is due to two main causes: photoreactivation and induction of synthesis of shielding pigments (flavonoids and cultivar waxes). Flavonoids absorb UV-B radiation and thus form an effective protective filter. In this sense, NO proved to increase the content of flavonoids and anthocyanins after UV-B irradiation in potato. Therefore, NO could be helpful in protecting crops against fluctuating and sometimes deleterious levels of UV-B radiation.

Under low irradiance environmental conditions the leaves of corn plants have shown evident symptoms of chlorosis. The treatment of such plants with weekly applications of SNP, by aspersion and/or irrigation, have reversed the lack of chlorophyll and increased the content of dry matter in the plants in a 10% as compared to the control plants. By applying the method of the invention extensive cultures may be carried out in geographic areas and zones with low irradiance. The nitric oxide (NO) promotes and stimulates the synthesis of chlorophyll which effects leads to a higher content of same even with low irradiance, in zones with a high number of cloudy days, for example. Furthermore, the application of NO provides energy savings particularly in green house cultures because the periods of artificial light necessary to supplement natural light in the green house may be reduced.

In wheat plants maintained in darkness for 8 days the treatment of such plants with SNP according to the invention, after such dark period, caused the chlorophyll content of the plants increase in a 30–40% as compared to control plants, that is plants not treated according to the invention.

The treatment of lettuce seeds (Lattuca sativa sp. Var. Grand Rapids) with NO promoted germination when these seeds were allowed to germinate under lack of ligth and under a temperature of 26° C. Furthermore, the SNP was more effective than the giberellic acid (GA3) in causing the seeds to germinate in darkness, (50% vs. 10% in germinated seeds). These percentages are specially meaningful if it is taken into account that the GA3 it is considered as being the most important germination promoter for the lettuce seeds in lack of light conditions.

It is also important to remark that there is another type of stress that is generated by the handling of the plants, particularly those plants cultured in intensive scale, in green houses, nurseries, and under artificial growing conditions. For example, in cultures carried out in vitro to produce callus and subsequent plantlets, the vegetable tissue is stressed.

The plants under culturing in greenhouses are subject to stress conditions and, in fact, result stressed because many species are regenerated through stem cutting wherein this regeneration comprises several steps and stages involving pot-to-pot transferences or transplantations until the plant is rooted and reaches the enough height to be transplanted in the field.

The treatment of potato (plantlets) with NO by irrigation or aspersion increased the yield of the mini tubers (Atlantica species) from plants cultured in greenhouses. The contents of chlorophyll and the leaves mass of the plants treated with NO were 20% higher as compared to the control plants.

The treatment according to the method of the invention has also increased the rooting and growing rate of lavender from stem cutting (Lavanda dentata) which increasement was evaluated based in the shoot size (leaves and roots) in the stem cutting, as well as based in the surviving of the plants after transplantation to the field.

The NO to be used in the invention can also be generated into solution by chemical reactions. In this sense, very good results were obtained with a mixture of 100 $\mu$M ascorbic acid and 200 $\mu$M sodium nitrite, which in an acidified medium generate NO. The low cost of these reactants makes this alternative a good NO source for application to crops.

An NO solution can be used for watering or spraying cultures. The inventors have obtained very good results when NO donors have been used to spray plants together with a coadyuvant (e.g. Sandowet, Novartis) at a concentration of 0.2% (0.5 mg ml-1 of solution). For spraying, the inventors employed a symmetrical KNSPSACK sprayer plus 16 (Guarany) having a Universal nozzle with a locking nut to facilitate the fitting of the directional shield for NO application.

The invention will be now further explained and disclosed by consideration of the following purely exemplary and non-limiting examples.

EXAMPLE 1
Resistance to Chilling in Tomato Plants.

Twenty days old tomato plantlets (*Lycopersicum esculentum* sp.) were transplanted from a seedbed to individual pots by using sterile soil as support. Three plants were placed in each pot and the pots were placed in rooms at a temperature of 25° C., with a photoperiod of 14-h and irradiance of 200 $\mu$E m$^{-2}$ s$^{-1}$. The pots were treated according to the invention by aspersion of several solutions: a) Sodium nitroprusside 100 $\mu$M (SNP), b) NO$_2$Na plus NO$_3$Na, 10 $\mu$M each one, and c) H$_2$O. The treatments b) and c) are controls. After 24 hours of pre-treatment the pots were placed into a cold chamber at 4° C., with a photoperiod of 14 h and an irradiance of 200 $\mu$E m$^{-2}$ s$^{-1}$. The pots were placed in individual boxes and treated weekly with the above indicated solutions. After 90 days maintained under the above conditions it was observed that the tomato plants treated with SNP remained in a stationary state. When transferred to a room at 18° C. the plants recovered and completed their cycle.

The tomato plants treated as control plants did not survive to the 90 day treatment at 4° C. and no shoots were seen even when the plants had subsequently been cultured at 18° C.

EXAMPLE 2
Resistance to Chilling in Wheat and Corn Plants.

Five days old wheat plantlets and 8 days old corn plantlets were grown in 14 cm. diameter pots containing a mixture of soil/vermiculite (3:1), with a photoperiod of 14-h and an irradiance of 200 $\mu$E m$^{-2}$ s$^{-1}$ at 25° C. The culture density was 40 wheat plants per pot and 3 corn plants per pots. The individual pots were treated with several treatments according to the invention by irrigation and aspersion of 100 ml of the following solutions: a) Sodium nitroprusside 100 $\mu$M (SNP), b) NO$_2$Na plus NO$_3$Na, 10 $\mu$M each one, and c) H$_2$O. The treatments b) and c) were carried out as controls. After 36 hours of the treatment the pots were placed into a cold chamber at −4° C. and darkness. The wheat plants remained at that temperature during 20 hours and the corn plants were kept at such temperature for 3 hours before transferring the plants to culturing chambers with photoperiods of 14 hours at 18° C. The time taken by the plants treated with SNP to recover after the chilling period was shorter than the time taken by the non treated plants (controls). The results shown that after 10 days from the stress under chilling, at 25° C. and with a photoperiod of 14 hours, the treated plants developed leaf areas 50% larger than the leaves of the control plants.

EXAMPLE 3
Resistance to Hydric Stress in Wheat Plants.

Six wheat plantlets per 18 cm. diameter pot were cultured during 20 days in vermiculite, in a room having a photoperiod of 14-h and an irradiance of 200 $\mu$E m$^{-2}$ s$^{-1}$ at 25° C. Each pot was irrigated with Hoagland complete solution 100 ml, plus 50 ml of the following solutions: a) 100 $\mu$M Sodium nitroprusside (SNP), b) NO$_2$Na plus NO$_3$Na, 10 $\mu$M each one, and c) H$_2$O. The treatments b) and c) were carried out as controls. Furthermore, 50 ml of the same solution were applied by aspersion to the pots. At the 12$^{th}$ day the irrigation was interrupted and the pots remained under the same temperature and light conditions. The plants did not receive any treatment for 15 days and at the end of the 15 days the plants shown signs of permanent withered condition. At that moment all the pots were irrigated again with Hoagland solution at a saturation point. After 10 days of irrigation the plants treated according to the invention with SNP shown clear recovering symptoms with their leaves becoming green or verdant again as from their meristematic areas. The recovery of the control plants were remarkedly delayed.

The plants were subsequently passed to 20 cm diameter pots containing soil, they were irrigated with water and kept under the same above light and temperature conditions. In all the cases the hydric stress determined a shortening in the normal cycle of the plant, thus rapidly enterin the flowering stage and grain formation.

After three months the plants completed their cycles and were harvested. The count of spikes and grains in the plants showed that the plants treated according to the invention had 50% more grains and spikes than the non treated plants.

EXAMPLE 4
Resistance to UV Irradiation in Potato Leaves.

Potato plants (*Solanum tuberosum* sp. cv. Pampeana) were cultured in pots containing a mixture of soil/vermiculite (3:1) for 30 days in a culturing room with a 14-hours photoperiod and at a temperature of 25° C. Whole and fully developed leaves were excised and inserted in tubes containing: a) 100 $\mu$M Sodium nitroprusside (SNP), or b) H$_2$O. The tubes containing the leaves were inserted into a vacuum chamber and the solutions absorption was induced by two vacuum shots each one of 10 seconds. Then, the leaves were transferred to the culturing room and were kept in the room for 24 hours (pre-treating) under the same above light and temperature conditions. After the pre-treatment the leaves were subject to UV radiation for 30 minutes, with the UV radiation applied to the adaxial face of the leaves, this irradiation being carried out with a trans-illuminator having 4 tubes of 15 watts and 300 nm transmitted wavelength. The necrotic and chlorotic injuries in the folioles were determined at several times after the UV light application. After 48 hours of the UV irradiation 50% more healthy tissue was found in the leaves treated with SNP as compared to the control leaves.

At the same time, an extraction of antocianines and flavonoids was carried out in the several samples and the contents of these pigments were determined by an absorption spectra between 450–600 nm wavelengths for the antocianines and between 250–450 nm wavelengths for the flavonoids. Along the entire analyzed spectra increased levels of the pigments wre found in the leaves treated with SNP as compared to the control leaves, the most remarked differences being found in some spectra regions of flavonoids, where more than the 80% in the pigment contents have been found in the leaves pre-treated with SNP as compared to the control leaves.

EXAMPLE 5
Increasing of the Chlorophyll Content in Corn Leaves Growing Under Low Irradiance.

Three hybrid Canner, sweet corn plants (*Zea mays* sp.) were grown in 12 cm diameter pots containing a mixture of soil/vermiculite (3:1). The pots were placed in rooms with a 14-h photoperiod and an irradiance of 200 $\mu E$ m$^{-2}$ s$^{-1}$ at 25° C. Under those growing conditions the corn plantlets developed the following characteristics: as from the third leaf the mesophyll cells, corresponding to the mesophyll region, shown evident chlorosis symptoms with remarked yellow longitudinal strips. This chlorosis is reminiscent of the lack-of-iron phenotype (mutants ys1 and ys2). This lack of chlorophyll was reverted by weekly applications of 10 ml of 100 $\mu M$ SNP per plant. The SNP was applied by spraying and/or irrigation (1:1). The SNP applications started in the second leaf stage. Fourty five days after the seed planting the corn plants treated with SNP contained 40%±10% more chlorophyll and 10% more dry matter as compared to the non treated plants.

EXAMPLE 6
Increasing of the Productive Yielding in Potato Mini-Tubers.

The productive yield of potato mini-tubers from plants grown in greenhouses during winter (average temperature: day=12° C.; night=4° C.; average luminosity: light during 9 hours; intensity: 150 $\mu E$ m$^{-2}$ s$^{-1}$) is markedly below the yields obtained in springtime and summer. Virus-free potato plants (Atlantic variety) from in vitro cultures were placed in pots containing sterile soil, in the growing stage corresponding to 6 leaves and a 6 cm length stem. Two treatments have been carried out (irrigation and aspersion) in groups A, B, C and D, each group comprising 70 pots. Group A and B comprised plants after 45 days and 15 days after transplantation, respectively. These plants were treated by aspersion. Groups C and D with 45 and 15 days old plants, respectively, received irrigation. The treatments consisted in two applications (each one spaced 15 days from the other) of 5 liters 100 $\mu M$ SNP in each group comprising 70 pots. Other 4 groups, also comprising 70 pots each, received water (control) under the same conditions. Each pot containing two potato plants received an average 2 mg SNP dissolved in water. The potatos mini-tubers were harvested at the end of their growing cycle (at the end of August). The results shown that the chlorophyll content (determined by measuring its absorbance at 652 nm) and the leaves mass were 30% higher in the plants aspersed with SNP and 20% higher in the plants irrigated with SNP as compared to the control plants. In turn, the plants treated with SNP had a mini-tubers average production 30% higher than the control plants.

EXAMPLE 7
Increasing of the Rooting Rate and Growing Rate in Lavender Stem Cutting.

Lots of 300 lavender stem cutting (*lavanda dentata*) placed in greenhouses, in 40 cm×50 cm trays containing perlite as inert support, were aspersed for three days before placed in individual pots containing soil and transferred to the field. The aspersion consisted of the application of 500 ml 100 $\mu M$ SNP per tray. The control trays were aspersed with water. Three days after the treatment the plants were transferred to the field (hibernation station). A second and a third application with 1 liter 100 $\mu M$ SNP per lot of 300 pots, at 7 and 15 days, respectively, were carried out after transplantation of the plants to the field. The shoots sizes in the stem cutting and the survival after transplantation were measured, with the results being shown in Table 1.

TABLE 1

| | Stem Height (cm) after-treat. (days) | | | Increase (%) | Survival (%) |
|---|---|---|---|---|---|
| | 7 | 15 | 22 | 7–22 | 22 |
| SNP | 8.8 ± 2 | 10 ± 2 | 11.7 ± 2.5 | 33 | 93 |
| H$_2$O | 7.1 ± 2 | 7.3 ± 2 | 7.5 ± 2 | 6 | 73 |

The treatment with SNP increased the size of the stem cutting shoots and the percentage of plants that survived to the handling during the several and successive transplantation.

EXAMPLE 8
Germination of Seeds in Light-Depending Processes.

The germination of lettuce seeds (*Lattuca sativa* sp. var. Grand Rapids) is light-depending at temperatures above 25° C. However, at that temperature but without light the seeds germinate in a normal pattern only if the seeds are kept on a filter wet in a solution containing 100 $\mu M$ SNP or 100 $\mu M$ SNAP (s-nitroso-N-acetyl penicillamine). Furthermore, the germination is inhibited if under such conditions a specific nitric oxide scavenger is added such as Carboxi-PTIO (potassium salt of 2-(4-carboxy-phenyl)-4,4,5,5-tetramethyllimidazoline-1-oxyl-3-oxide). Ii has been found that in the var. Grand Rapids subject to these essays the light may be replaced by a treatment with giberelic acid (GA$_3$) 100 $\mu M$ SNP. It has been observed, however, in parallel essays, that in 100 seeds placed to germinate in darkness at 26° C., the SNP was more effective than the GA$_3$. While the 10 $\mu M$ SNP promoted the germination of 50% of lettuce seeds, germination with 10 $\mu M$ GA$_3$ only reached to 10% of the seeds.

EXAMPLE 9
Increasing of Chlorophyll Levels in Wheat Growing in Darkness.

Wheat plantlets were grown in pots containing a mixture of soil/vermiculite (3:1), at 18° C. and under total darkness. Several pots were subject to different treatments: a) 100 $\mu M$ Sodium nitroprusside (SNP), b) NO$_2$Na plus NO$_3$Na, 10 $\mu M$ each one, or c) H₂O. The treatments b) and c) were carried out as controls. Several pots containing 15 wheat plantlets were aspersed and irrigated with 50 ml solution a), b) or c) and kept in isolated and ventilated chambers at 18° C. and in darkness. After 8 days the chlorophyll was extracted from the plantlets leaves that had been treated according to the invention and the chlorophyll content was determined by measuring the absorbance at 652 nm. The treatment with SNP resulted in a 30–40% increasing of chlorophyll as compared to the values obtained in the control plants.

The chlorophyll level increase by use of SNP was also synergized by subjecting the plants to other factors but keeping the same above conditions. Only one 2-h pulse of white light (200 $\mu$E m$^{-2}$ s$^{-1}$) increased the chlorophyll level in the plants treated with SNP a 70% above the levels of the control plants.

In other essays, the application of daily 2-h pulses of light during 7 days increased the chlorophyll levels in a 150%. In other essays also was observed: 1) mechanical injury or damage (wounding) and 2) infection with wheat pathogens (*Septoria tritici* sp.), independently achieved an increase of the chlorophyll levels in the leaves treated with SNP, wherein the increase was 250–300% above the control plants.

EXAMPLE 10
Resistance to Chilling in the Germination Process of Sweet Corn.

Sweet corn grains (*Zea mays* sp. Hybrid Canner) were placed in germinators at a temperature of 25° C., with a 14-h photoperiod and an irradiance of 200 $\mu$E m$^{-2}$ s$^{-1}$.

Several germinators were wet with several solutions: a) 100 $\mu$M Sodium nitroprusside (SNP), b) NO₂Na plus NO₃Na, 10 $\mu$M each one, or c) H₂O. The treatments b) and c) were carried out as controls. Each 6 days at 5° C., the germinators were placed for 1 day in a chamber with the same above photoperiod but at 18° C. After 10 days all the grains showed the radicle emergence and the hypocotyl appearance. However, after 30 days of the beginning of the essays, while the grains germinating in NO₂⁻/NO₃⁻ and H₂O showed a paralyzation in the germination process together with a withered condition in the radicle and the hypocotyl, the grains germinating in SNP continued growing and reached radicle lengths of 5 cm±0.5 cm and hypocotyl lengths of 1 cm±0.3 cm. These values were similar to those reached by hybrid hard corn commercialized by the firm Dekalb as DK615 and DK696 and placed to germinate in identical conditions.

EXAMPLE 11

Resistance to Methylviologen Herbicides and Other Compounds Generating Reactive Oxygen Species (ROS).

30 years old potato plants were grown in a mixture of soil/vermiculite (3:1) at 25° C., with a 14-h photoperiod and an irradiance of 200 $\mu$E m$^{-2}$ s$^{-1}$, aspersed with 50 ml/day solution of 100 $\mu$M SNP, for two days. The control plants were aspersed with H₂O. At the third day, the plants were aspersed with a diluted solution Diquat (2 mg L$^{-1}$). The Diquat is a total herbicide that interrupts the photosynthetic electron transport chain, thus promoting the super-oxide generation and destruction of photosynthetic membranes and chlorophyll. The macroscopic result from the application of Diquat on the leaves is a remarked chlorosis in the leaves and the stem of the plant, as well as dessication and defoliation. The pre-treated potato plants resisted the herbicide action and remained like the control plants not treated with the herbicide.

In addition to the above, the SNP was also capable of protecting the potato leaves sprayed with Diquat or Paraquat from damaging processes leading to molecular injuries such as chlorophyll looses, lipid peroxidation, ion looses, protein decay, RNA decay, including cellular dead, thus considerably delaying the development of the symptoms from the treatment with the herbicide.

EXAMPLE 12
Protection of Potato Leaves Against Damaging Effects from the Pathogen Fungus Phytophthora Infestans.

Leaves from potato plants (*Solanum tuberosum* sp. Cv. Pampeana) grown for 30 days at 25° C. were floated in solutions containing: a) 100 $\mu$M Sodium nitroprusside (SNP), b) a mixture of 100 $\mu$M ascorbic acid +200 $\mu$M NO₂Na, that releases NO in solution at 5 pH, c) NO₂Na plus NO₃Na, 10 $\mu$M each one, or d) H₂O. The treatments c) and d) were carried out as controls. Two sets of the above conditions were used for treatment with: 1) a suspension of 10³ ml$^{-1}$ of sporangia of *P. infestans* and 2) without the fungus. After three days the leaves infected with *P. infestans* showed a large number of necrotic lesions, similar to those ones from cellular death. Said lesions were not found in the infected leaves that had been pre-treated with solutions a) or b). A diminishing ion leakage and DNA fragmentation was also observed.

In the following days the fungus mycelium begun to be seen on the infected leaves, for all of the treatments, i.e. in the presence or absence of NO donors. However, the injury produced by the infection was delayed by the NO, thus diminishing the chlorophyll looses. Chlorophyll quantification was performed by measuring Abs$_{652nm}$, considering that Chl ($\mu$g mL$^{-1}$)=27.7 A$_{652nm}$.

EXAMPLE 13
Chlorophyll Retention in Potato Leaves Subject to Hydric Stress.

Potato folioles (*Solanum tuberosum* var. Pampeana) were excised in approximately 1 cm² sections and placed in petri dishes containing the following solutions: a) 10 ml H₂O, b) 10 ml 100 $\mu$M SNP, c) 10 ml Polyethylen glycol (PEG) 8.000 at 30% (this condition being used to simulate a hydric deficit in the plants) or d) 10 ml PEG at 30% plus 100 $\mu$M SNP. The dishes were placed in an incuvation room at 25° C. with a 14-h photoperiod. Then, extractions of chlorophyll were performed each 24 hours for each treatment and quantifications were done by spectrometry by measuring absorbance 652 nm. The results of three independent essays showed that under hydric stress simulated by PEG 30% the chlorophyll levels due to the NO application remained above the levels of the controls, independently of the time extension of the treatment (see Table 2 wherein the chlorophyll is indicated as a % of the initial value).

TABLE 2

|  | Chlorophyll (%) Time of treatment (days) | | |
| --- | --- | --- | --- |
|  | 1 | 2 | 3 |
| H₂O | 100% ± 6 | 98% ± 1 | 86% ± 4 |
| SNP | 97% ± 12 | 97% ± 2 | 82% ± 8 |
| PEG | 87% ± 11 | 57% ± 20 | 48% ± 15 |
| PEG + SNP | 90% ± 5 | 91% ± 3 | 81% ± 1 |

While preferred embodiments of the present invention have been illustrated and described, it will be obvious to those skilled in the art that various changes and modifications may be made therein without departing from the scope of the invention as defined in the appended claims.

We claim:

1. Method of enhancing the metabolic function and the growing conditions of plants under culturing, plantlets, stem cutting, and seeds, wherein the dry matter and the productive yield and the chlorophyll yield of the plant is increased, the germinating capacity of the seed is enhanced, and root formation of the stem cutting is enhanced, the method comprising the step of contacting the plant, or the stem cutting, or the seed with nitric oxide.

2. The method of claim 1, wherein the plant is cultivated in a manner selected from extensive culturing and intensive culturing in a green house.

3. The method of claim 1, wherein the plant is selected from a plant obtained by micropropagation, a plant from a stem cutting, a plant from slips and a genetically modified plant.

4. The method of claim 1, wherein the plant is under oxidative stress conditions.

5. The method of claim 4, wherein the stress conditions are selected from: drought, dry season, water scarcity, salinity, herbicides, temperatures between 0–5° C., temperatures under 0° C., high temperatures, low irradiation, mechanical damage, UV irradiation and infection by organisms.

6. The method of claim 5, wherein the infecting organisms are selected from virus, bacteria and fungus.

7. The method of claim 5, wherein the herbicides are from the methyl viologen herbicides.

8. The method of claim 1, wherein the step of contacting the seed with the nitric oxide is carried out by one or more of the following: immersion, aspersion, fumigation, irrigation and soil fertilization.

9. The method of claim 1, wherein the nitric oxide is provided by NO releasing chemicals.

10. The method of claim 9, wherein the NO releasing chemicals are selected from sodium nitroprusside, ascorbic acid plus sodium nitrite, S-nitroso-N-acetylpenicillamine (SNAP), S-nitrosoglutathione and spermine-NO.

11. The method of claim 1, wherein nitric oxide is present in a concentration of about 10 nM to 1 $\mu$M.

12. The method of claim 1, wherein the step of contacting the plant with the nitric oxide is carried out by one or more of the following: aspersion, fumigation, irrigation and soil fertilization.

13. The method of claim 9, wherein the NO releasing chemicals are combined with wetting agents.

14. The method of claim 1, wherein the plant is selected from monocotyledon, dicotyledon and gymnosperm plants.

15. The method of claim 1, further comprising the step of germinating the seed after the contacting step.

16. The method of claim 1, wherein the seeds are germinated under one or more of the stress conditions selected from the group consisting of drought, dry season, water scarcity, salinity, herbicides, temperatures, low irradiation, mechanical damage, UV irradiation and infection by organisms.

* * * * *